United States Patent
Shalaby et al.

(10) Patent No.: US 8,034,850 B2
(45) Date of Patent: *Oct. 11, 2011

(54) SELF-SETTING ABSORBABLE COMPOSITES AND APPLICATIONS THEREOF

(75) Inventors: Shalaby W Shalaby, Anderson, SC (US); Michael Aaron Vaughn, Greenville, SC (US)

(73) Assignee: Poly-Med, Inc., Anderson, SC (US)

( * ) Notice: Subject to any disclaimer, the term of this patent is extended or adjusted under 35 U.S.C. 154(b) by 499 days.

This patent is subject to a terminal disclaimer.

(21) Appl. No.: 11/601,994

(22) Filed: Nov. 20, 2006

(65) Prior Publication Data

US 2007/0123603 A1   May 31, 2007

Related U.S. Application Data

(60) Provisional application No. 60/739,996, filed on Nov. 28, 2005.

(51) Int. Cl.
*A61K 6/083* (2006.01)
*C08K 3/32* (2006.01)
*A61K 33/42* (2006.01)

(52) U.S. Cl. ......... 523/115; 523/116; 424/602; 524/414

(58) Field of Classification Search .................. 523/115, 523/116; 424/602; 524/414
See application file for complete search history.

(56) References Cited

U.S. PATENT DOCUMENTS

| | | | |
|---|---|---|---|
| 3,896,077 A * | 7/1975 | Leonard et al. | 523/177 |
| 4,192,021 A * | 3/1980 | Deibig et al. | 623/23.61 |
| 4,202,055 A * | 5/1980 | Reiner et al. | 623/23.57 |
| 4,713,076 A * | 12/1987 | Draenert | 623/23.6 |
| 5,350,798 A | 9/1994 | Linden et al. | |
| 5,508,352 A | 4/1996 | Sasaki et al. | |
| 5,605,713 A * | 2/1997 | Boltong | 427/2.1 |
| 5,874,509 A | 2/1999 | Shalaby et al. | |
| 6,206,957 B1 * | 3/2001 | Driessens et al. | 106/35 |
| 6,379,453 B1 | 4/2002 | Lin et al. | |
| 6,616,698 B2 * | 9/2003 | Scarborough | 623/23.51 |
| 6,699,940 B2 | 3/2004 | Shalaby | |
| 6,723,114 B2 * | 4/2004 | Shalaby | 606/214 |
| 2005/0283255 A1 * | 12/2005 | Geremakis et al. | 623/23.51 |

FOREIGN PATENT DOCUMENTS

JP   2005146017 A  *  6/2005

OTHER PUBLICATIONS

Park et al., "Bioactive Cyanoacrylate-based Filling Material for Bone Defects in Dental Applications", Bioceramics 17, Trans Tech Pubmications, Switzerland, Key Engineering Materials vols. 284-286 (2005) pp. 933-936.*

Table of Contents, Bioceramics 17, p. 933, 2005, Trans Tech Publications Inc., Switzerland.*

* cited by examiner

*Primary Examiner* — Tae H Yoon
(74) *Attorney, Agent, or Firm* — McCormick, Paulding & Huber LLP

(57) ABSTRACT

Self-setting, bioactive, absorbable composites are derived from inorganic phosphate microparticles and a cyanoacrylate matrix of a methoxypropyl cyanoacrylate at a weight to volume ratio of at least 20/80 of microparticles/matrix. The self-setting composites are capable of the controlled release of bone mineralizing ions, antimicrobials, and bone growth promoters. Such composites are useful as bone cements, fillers, and/or substitutes.

15 Claims, No Drawings

SELF-SETTING ABSORBABLE COMPOSITES AND APPLICATIONS THEREOF

CROSS-REFERENCE TO RELATED APPLICATIONS

The present application claims the benefit of prior provisional application Ser. No. 60/739,996, filed Nov. 28, 2005.

FIELD OF THE INVENTION

The present invention relates to a new type of self-setting, absorbable, bioactive composites which can be used in their flowable, fast-curable form or as micromachined preformed blocks in prophylactic or reconstructive dental and orthopedic applications. More specifically, the present invention is directed toward self-curing, composite precursors made of one or more liquid cyanoacrylate monomer, and may also contain at least one absorbable or miscible polymer as a viscosity and/or absorption modifier and one or more inorganic phosphate-based types of microparticulates as a reinforcing agent. The bioactivity of the composites subject of this invention is due primarily to the ability of the composites to release, at a controlled rate, inorganic ions necessary for bone mineralization, namely $(PO_4)^{-3}$ and $Ca^{+2}$. Other imparted bioactivities are related to additives in the composites capable of having antimicrobial, anti-inflammatory, and bone growth promoting effects.

BACKGROUND OF THE INVENTION

The prior art most pertinent to the present invention deals with (1) cyanoacrylate-based absorbable tissue adhesives; (2) absorbable phosphate glasses; (3) resorbable calcium phosphate cement (CPC); and (4) polymeric methyl methacrylate/calcium phosphate-based composites. The absorbable cyanoacrylate-based tissue adhesives were disclosed by this inventor and coworkers in U.S. Pat. Nos. 5,350,798; 6,699,940; and 6,723,114, directed primarily to liquid systems of a methoxyalkyl cyanoacrylate containing a polymeric modifier to improve absorption and compliance of the cured adhesive. The adhesives were described as useful for soft tissue repair.

Also, pertinent to the present invention are the absorbable phosphate glasses which were disclosed by the present inventor and coworkers in U.S. Pat. No. 5,874,509, directed to surface-activated calcium phosphate glasses, preferably made using, in part, $ZnO$ or $SiO_2$, wherein surface activation entailed indirect grafting (through reactive intermediate functional groups) absorbable aliphatic polyester chains to provide improved adhesion to an absorbable polymeric matrix when used in forming absorbable phosphate thermoplastic composites.

A resorbable CPC composition was disclosed in U.S. Pat. No. 6,379,453 and was described as a self-setting inorganic bone cement. In spite of its ease of application, the CPC suffers from being fragile and highly susceptible to fracture under normal physiological stresses when used as a bone cement.

Also pertinent to the present invention are the polymeric methacrylate/calcium phosphate composites disclosed in U.S. Pat. No. 5,508,342 which deals with bioactive compositions and solid composites formed therefrom. These composites were noted as being able to provide sufficient sustained and timed release levels of $Ca^{+2}$ and $(PO_4)^{-3}$ ions which can provide long-term protection against demineralization and promote mineralization of contiguous skeletal tissue. Accordingly, such composites were expected to have wide application as prophylactic, adhesive, prosthetic, and restorative materials, particularly in the field of dentistry.

Unfortunately, the prior art described above failed to identify an absorbable composite that has the integrated attributes of the (1) absorbable cyanoacrylate tissue adhesives, (2) high modulus phosphate-based microparticles as fillers in a thermoplastic matrix, and (3) absorbable phosphate glasses and their use as soluble or partially soluble calcium phosphate-based microparticles, capable of the controlled release of bioactive ions needed for bone mineralization, namely, $(PO_4)^{-3}$ and $Ca^{+2}$. The perceived clinical significance of these integrated attributes provided an incentive to pursue the present invention which deals with a new type of self-setting absorbable, bioactive, polymeric, cyanoacrylate composite based on flowable precursors comprising water-soluble or partially water-soluble calcium-phosphate solid microparticulates in a liquid cyanoacrylate-based matrix.

SUMMARY OF THE INVENTION

Accordingly, the present invention is directed to an absorbable, self-setting, bioactive composite having at least 20 percent weight/volume of inorganic phosphate microparticles in a polymeric cyanoacrylate matrix. Preferably, the cyanoacrylate is a methoxyalkyl cyanoacrylate, most preferably methoxypropyl cyanoacrylate. In another preferred embodiment the cyanoacrylate is a mixture of an alkyl cyanoacrylate and an alkoxyalkyl cyanoacrylate. For such embodiment it is preferred that the alkyl cyanoacrylate is ethyl cyanoacrylate and the alkoxyalkyl cyanoacrylate is methoxypropyl cyanoacrylate.

The inorganic phosphate microparticles of the present inventive composite may be selected from anhydrous dibasic calcium phosphate ($CaHPO_4$), calcium pyrophosphate ($Ca_2P_2O_7$), essentially dry calcium phosphate cement (CPC), essentially dry amorphous calcium phosphate, a reaction product of calcium pyrophosphate and calcium carbonate having the molecular formula $Ca_4(PO_4)_2O$, essentially dry tricalcium phosphate ($Ca_3(PO_4)_2$), essentially dry octaphosphate, dry basic calcium phosphate ($3Ca_3(PO_4)_2 \cdot Ca(OH)_2$), dry hydroxyapatite ($Ca_{10}(PO_4)_6(OH)_2$), monobasic calcium phosphate ($Ca(H_2PO_4)_2$), $Ca_5(PO_4)_3OH$, and a phosphate glass derived from $CaO$, $P_2O_5$, and at least one oxide selected from the group consisting of $K_2O$, $Na_2O$, $ZnO$, and $SiO_2$. Preferably, the inorganic phosphate microparticles are anhydrous dibasic calcium phosphate, which may be blended with other inorganic phosphate microparticles such as $K_2HPO_4$, $KH_2PO_4$, $Na_2HPO_4$, $NaH_2PO_4$, or an absorbable phosphate glass derived from $CaO$, $P_2O_5$, and at least one oxide such as $K_2O$, $Na_2O$, $ZnO$, and $SiO_2$. Alternatively, the inorganic phosphate microparticles may be dry basic calcium phosphate ($3Ca_3(PO_4)_2 \cdot Ca(OH)_2$), which may be blended with $K_2HPO_4$ or $KH_2PO_4$. However, in a most preferred embodiment the inorganic phosphate microparticles are anhydrous dibasic calcium phosphate which comprise from about 20 percent to about 90 percent weight/volume of the total composite.

Preferably, the present inventive composite further includes at least one absorbable viscosity/absorption polymeric modifier such as copolyesters of cyclic lactones, polyalkylene carbonates, polyalkyl cyanoacrylates, copolymeric cyanoacrylates, or polymeric alkoxyalkyl cyanoacrylates.

In one preferred embodiment the inorganic phosphate microparticles are capable of the controlled release of $(PO_4)^{-3}$ and $Ca^{+2}$ for promoting bone mineralization. In another preferred embodiment the inorganic phosphate microparticles are capable of the controlled release of $Zn^{+2}$ for accelerating bone growth.

Preferably, the present inventive composite includes at least one bone growth promoter such as bone morphogenic protein (BMP), fibroblast-derived growth factors (FGF), and functionally similar oligopeptides or recombinant products.

It is also preferred that the present composite includes at least one bioactive agent such as antimicrobial agents or anti-inflammatory agents.

The present composite is useful for a variety of end use applications including those involving tooth sockets, non-union bones, bone prostheses, osteoporotic bones, intervertebral spaces, alveolar ridges, facial and cranial fracture and defects, internal fracture fixation, artificial joint replacement, and infected bones.

It is preferred that the inventive composite has a weight average molecular weight exceeding 300 kDa and that the inorganic microparticles are covalently linked at least at their surfaces to the polycyanoacrylate chain.

A key aspect of this invention deals with the incorporation of polymeric microparticles which are intended to accelerate or mediate the anionic polymerization of the cyanoacrylate constituents of the self-setting bioactive composite. More specifically, this invention deals with an absorbable, self-setting, bioactive composite comprising at least 20 percent weight/volume of inorganic phosphate microparticles in a polymeric cyanoacrylate matrix, which further comprises polymeric microparticles for mediating the anionic polymerization of the cyanoacrylate monomer(s), wherein the microparticles comprise a carboxy-terminated polyglycolide. Another specific aspect of this invention deals with an absorbable, self-setting, bioactive composite comprising at least 20 percent weight/volume of inorganic phosphate microparticles in a polymeric cyanoacrylate matrix, which further comprises at least one type of polymeric microparticles capable of accelerating the anionic polymerization of the cyanoacrylate monomer(s) wherein the microparticles comprise hydroxy-terminated polyglycolide or chitosan. In addition to its use as a polymerization accelerator, chitosan is used to promote bone regeneration.

DETAILED DESCRIPTION OF PREFERRED EMBODIMENTS

The present invention is directed to a new family of self-setting absorbable polymeric cyanoacrylate composite systems which offer unexpectedly novel structural and biological properties that differ from those associated with the absorbable cyanoacrylate tissue adhesives used primarily for repairing soft tissue defects. And this invention is directed toward self-setting absorbable composite precursors comprising an anionically polymerizable alkyl and/or alkoxyalkyl cyanoacrylate monomer, and one or more absorbable or soluble phosphate microparticulate reinforcing agents, which can directly or indirectly catalyze the anionic polymerization of the cyanoacrylate monomers. To modulate the properties of the composite to meet specific application requirements, absorbable polymeric modifiers are incorporated in the liquid monomer(s) prior to use. These modifiers can be selected from the group represented by polyalkoxyalkyl cyanoacrylate, polyalkyl cyanoacrylates, copolymeric cyanoacrylates, segmented polyether ester, polyaxial polyester-carbonates, a polyalkylene carbonate, and similar low melting temperature or amorphous polymers. The resulting composites are characterized by an unexpectedly high degree of toughness and can be readily formed at about 37° C. The high degree of toughness is, in part, associated with exceptionally high molecular weight of the anionically polymerized acrylate monomer(s), produced under the prevailing conditions. As orthopedic or dental implants, these composites can undergo gradual mass loss with concomitant release of bone mineralizing ions to assist in bone generation at the implant site. Because of the inherent adhesive properties of the cyanoacrylate-based matrix, the self-setting compositions adhere exceptionally well to the adjacent soft and bony tissues at the implant site, thus insuring early and initial post-operative implant mechanical stability. The composite precursors are flowable and can be easily extruded to the biological site to conform to any irregular geometry of the surrounding immediate area to form a solid adherent layer at the interface and provide a strong joint while the bulk of the composite develops its cohesive strength.

The composites, subject of this invention, can also be formed in the laboratory as solid blocks which can be micromachined into absorbable articles for internal bone fixation, such as bone plate and screws. The preformed blocks can also be micromachined into absorbable devices for use in reconstructive cranio-maxillofacial applications. Alternatively, these micromachined devices can be formed by casting uncured or partially cured flowable precursors of the subject composites into non-sticking molds of the required geometries.

Among the key applications of the partially cured or uncured flowable precursors of the composites subject of this invention are their uses as an adhesive cement for adjoining small broken bones and as adhesive cement in artificial joint replacement, wherein the composites adhere well to metallic (or ceramic) prostheses as well as the boney tissues. As such composites degrade, natural bone grows gradually towards the metallic (or ceramic) prosthesis and eventually forms an exceedingly strong interface, thus providing an outstanding mechanical stability immediately after implantation and during the entire life of the implant. Other applications include the present composite's use as an injectable root canal filler in dental applications, for glazing microporous dental enamel to prevent bacterial invasion and/or to minimize neural sensitivity to environmental changes about dental tissues, in sealing or filling cracks or carries in bones or teeth, in repairing skeletal defects and particularly in the cranio-maxillofacial region, and in repairing fractures or adjoining parts of the vertebral column.

A scientifically and technologically important aspect of this invention deals with the ability to polymerize the cyanoacrylate monomer(s) in the presence of the inorganic microparticulate components of the composite precursor, to produce exceptionally high molecular polymers under easily controlled thermal conditions, having a weight average molecular weight exceeding 300 kDa and 400 kDa (as determined by GPC using $CH_2Cl$ as a solvent) depending on the chemical structure of the inorganic components. Having an exceptionally high molecular polycyanoacrylate matrix allows the formation of a composite with exceptional mechanical properties, including an unusually high impact strength and fatigue endurance. This is most useful in applications when the composite is used in repairing or augmenting high modulus, load-bearing bony tissues. Another scientifically and technologically important aspect of this invention is related to the ability of inorganic fillers to initiate the polymerization of the cyanoacrylate monomer(s), leading to covalently linked chains of the organic matrix to the inorganic filler, and creating a hybrid interface between the composite components. Such unique intimacy of the filler and matrix contributes significantly to exceptionally high strength, impact resistance, and fatigue endurance. Depending on the chemical structure of the inorganic filler, its surface-to-volume ratio, and weight fraction in the composite precursor, the setting or curing time to a solid composite can vary from a few minutes to several hours. This broadens the scope of clinical applicability of these compositions, as they can be tailor-made to meet the specific requirements of several surgical procedures.

This invention deals generally with an absorbable, self-setting, bioactive, polymeric cyanoacrylate composite comprising at least 20 percent weight/volume of inorganic phosphate microparticles, wherein the cyanoacrylate is a methoxyalkyl cyanoacrylate as in methoxypropyl cyanoacrylate, and wherein the inorganic phosphate is anhydrous dibasic calcium phosphate ($CaHPO_4$) with the composite, precursor mixture comprising 10/90 and 90/10 volume/weight ratio of the cyanoacrylate monomer and anhydrous dibasic calcium phosphate, respectively, and the cyanoacrylate monomer comprises at least one absorbable viscosity/absorption, polymeric modifier selected from the group represented by copolyesters of cyclic lactones, polyalkylene carbonates, polyalkyl cyanoacrylates, copolymeric cyanoacrylates, and polymeric alkoxyalkyl cyanoacrylates.

One aspect of this invention deals with an absorbable, self-setting, bioactive, polymeric cyanoacrylate composite comprising at least 20 percent weight/volume of inorganic phosphate microparticles, wherein the cyanoacrylate comprises a mixture of an alkyl cyanoacrylate as in ethyl cyanoacrylate and an alkoxyalkyl cyanoacrylate as in methoxypropyl cyanoacrylate, and wherein the inorganic phosphate is anhydrous dibasic calcium phosphate ($CaHPO_4$), with the composite precursor mixture comprising 20/80 and 80/20 volume/weight ratio of the cyanoacrylate monomer and anhydrous dibasic calcium phosphate, respectively, and the cyanoacrylate monomer comprises at least one absorbable viscosity/absorption, polymeric modifier selected from the group represented by copolyesters of cyclic lactones, polyalkylene carbonates, polyalkyl cyanoacrylates, copolymeric cyanoacrylates, and polymeric alkoxyalkyl cyanoacrylates.

Another aspect of this invention deals with an absorbable, self-setting, bioactive, polymeric cyanoacrylate composite comprising at least 20 percent weight/volume of inorganic phosphate microparticles, wherein the inorganic phosphate is one or more material selected from the group represented by anhydrous dibasic calcium phosphate ($CaHPO_4$), calcium pyrophosphate ($Ca_2P_2O_7$), essentially dry calcium phosphate cement (CPC), essentially dry amorphous calcium phosphate, a reaction product of calcium pyrophosphate and calcium carbonate having the molecular formula $Ca_4(PO_4)_2O$, essentially dry tricalcium phosphate ($Ca_3(PO_4)_2$), essentially dry octaphosphate, dry basic calcium phosphate ($3Ca_3(PO_4)_2.Ca(OH)_2$), dry hydroxyapatite ($Ca_{10}(PO_4)_6(OH)_2$), monobasic calcium phosphate ($Ca(H_2PO_4)_2$), $Ca_5(PO_4)_3OH$, and a phosphate glass derived from CaO, $P_2O_5$, and at least one oxide selected from the group consisting of $K_2O$, $Na_2O$, ZnO, and $SiO_2$.

A specific aspect of this invention deals with an absorbable, self-setting, bioactive, polymeric cyanoacrylate composite comprising at least 20 percent weight/volume of inorganic phosphate microparticles, wherein the inorganic phosphate microparticles comprising at least one of the following combinations: $CaHPO_4$/absorbable phosphate glass derived from CaO and $P_2O_5$ and at least one oxide selected from the group represented by $K_2O$, $Na_2O$, ZnO, and $SiO_2$; $CaHPO_4$/ $K_2HPO_4$; $CaHPO_4/KH_2PO_4$; $CaHPO_4/Na_2HPO_4$; $CaHPO_4/NaHPO_4$; $3Ca_3(PO_4)_2.Ca(OH)_2/K_2HPO_4$; and $3Ca_3(PO_4)_2.Ca(OH)_2/KH_2PO_4$.

Another specific aspect of this invention deals with an absorbable, self-setting, bioactive, polymeric cyanoacrylate composite comprising at least 20 percent weight/volume of inorganic phosphate microparticles, wherein the inorganic phosphate microparticles are capable of the controlled release of inorganic ions, such as $(PO_4)^{-3}$ and $Ca^{+2}$, for promoting bone mineralization and preferably the inorganic phosphate microparticles are capable of the controlled release of inorganic ions, such as $Zn^{+2}$, for accelerating bone growth.

A clinically important aspect of this invention deals with an absorbable, self-setting, bioactive, polymeric cyanoacrylate composite comprising at least 20 percent weight/volume of inorganic phosphate microparticles, with the composite comprising at least one bone growth promoter selected from the group represented by bone morphogenic protein (BMP), fibroblast-derived growth factors (FGF), and functionally similar oligopeptides and recombinant products.

Another clinically important aspect of this invention deals with an absorbable, self-setting, bioactive, polymeric cyanoacrylate composite comprising at least 20 percent weight/volume of inorganic phosphate microparticles, with the composite comprising at least one bioactive agent selected from those having antimicrobial and anti-inflammatory activities.

From an application perspective, this invention deals with an absorbable, self-setting, bioactive, polymeric cyanoacrylate composite comprising at least 20 percent weight/volume of inorganic phosphate microparticles, wherein the composite can be used in cranio-maxillofacial, dental, and orthopedic applications, as in those dealing with tooth sockets, nonunion bones, bone prostheses, osteoporotic bones, intervertebral spaces, alveolar ridges, facial and cranial fracture and defects, internal fracture fixation, artificial joint replacement, and infected bones.

From a processing perspective, this invention deals with a process for producing, under controlled thermal conditions, a polycyanoacrylate having a weight average molecular weight exceeding 300 kDa, and a process for direct production of inorganic microparticulates covalently linked at least at their surfaces to a polycyanoacrylate chain.

Further illustrations of the present invention are provided by the following examples:

EXAMPLE 1

Preparation and Characterization of Absorbable Phosphate Glasses: Typical Methods Preparation of these glasses requires the use of certain intermediate compounds which, upon heating in the early stages of glass formation produce their respective oxides, water vapor, carbon dioxide, and/or ammonia gas. This requires adjusting the initial stoichiometry of the glass precursors to account for the expected initial mass loss due to vapor or gas evolution and staging the heating process to prevent premature, uncontrolled gas evolution at the early stages of glass formation. An illustration of the changes in mass of typical gas- or vapor-producing starting compounds upon thermal conversion to their respective oxides is given below:

| Starting Compound | Vapor or Gas Evolved | Resulting Oxide |
|---|---|---|
| $K_2H_2PO_4$ | $H_2O$ | $P_2O_5$ |
| $Na_2H_2PO_4$ | $H_2O$ | $Na_2O, P_2O_5$ |
| $(NH_4)H_2PO_4$ | $H_2O, NH_3$ | $P_2O_5$ |
| $SiO_2 \cdot xH_2O$ | $H_2O$ (10.6 wt %) | $SiO_2$ |

To form these glasses, as per the teaching of U.S. Pat. No. 5,874,509, predetermined weights of the powdered starting components are thoroughly mixed and transferred into porcelain crucibles (Coors, 15 mL capacity) and heated in a Branstead Thermolyne-62700 muffle furnace from room temperature to 300° C. at a rate of approximately 10° C./min., followed by a heating rate of 15°/min. to reach 500° C. During this heating period, the mixture undergoes loss of water, carbon dioxide, and/or ammonia, depending on its composition. Melting then occurs between 700° C. and 1100° C. Once the melt appears clear and homogeneous (usually between 800-900° C.), the glass is poured onto a steel mold and annealed at 200° C. for 15-30 minutes and allowed to slowly cool to room temperature. Melts are preferably poured onto a stainless steel plate at the lowest temperature possible to reduce volatilization of $P_2O_5$.

For size reduction, the resulting glass is first ground at room temperature using a Wiley Mill and sieved to isolate two crops of particles having average diameters not exceeding 100μ and 500μ. The two crops are then subjected separately to cryogenic size reduction at liquid nitrogen temperature using a Spex 6850 Freezer Mill. In both cases, the size reduction is pursued for the required period of time to produce microparticles having the desired particle size distribution. The final products are isolated and dried at 60° C. under reduced pressure, prior to charactering and mixing as components of the precursors system.

The resulting glasses are characterized for (1) identity and composition using FTIR, elemental microanalysis, and electron spectroscopy for chemical analysis (ESCA); (2) thermal property and morphology using high temperature DSC and X-ray diffraction methods; and (3) particle size and particle size distribution and surface morphology using particle size analyzer and scanning electron microscopy.

EXAMPLE 2

Preparation of a Representative Calcium Phosphate Glass Composition, CaPG

Using the general method for glass formation, size reduction, and characterization as described in Example 1, calcium phosphate glass (GPC) having the following molar composition of the oxide precursors is produced: $P_2O_5$, 62%; $Na_2O$, 15%; CaO, 18%; ZnO, 5%

EXAMPLE 3

Formation and Characterization of 50/50 (Weight/Volume) $CaHPO_4$/Polymethoxypropyl Cyanoacrylate Composites (C-1)

Five grams of microparticulate dibasic calcium phosphate ($CaHPO_4$) predried at 130° C. for at least 3 hours were added, while stirring using a Teflon coated stirrer under dry nitrogen atmosphere, to 4 mL of methoxypropyl cyanoacrylate at room temperature. After mixing, the reactor was closed and transferred into a 37° C. incubator. After 10 hours, the cured composite was isolated and characterized for molecular weight of the methylene chloride-extracted polymer (using GPC) and weight loss of pre-cut sheets (about 2 mm thick and weighing about 83 to 404 mg) in deionizing water (10 mL) at 50° C. for 10 days. The GPC and weight loss data and associated decrease in pH of the supernatant aqueous medium are summarized in Tables I and II, respectively. For determining the weight loss, the specimens are removed from the aqueous medium, dried at 25° C. and then at 50° C. under reduced pressure until a constant weight is achieved.

TABLE I

Composition of Composite Precursors, Curing Conditions, and Weight Average Molecular Weight ($M_w$) of Polymeric Matrix

| Composite Number | Precursor Compositions | | Curing Conditions | | Polymeric Matrix |
|---|---|---|---|---|---|
| | Inorganics/ MPC Mg/mL | Weight Ratio of Inorganic Component | Temp/Time, ° C./Hour | | $M_w$, (kDa) |
| | | | Partial Curing | Full Curing | |
| C-1 | 50/50 | 100/0, $CaHPO_4$ | 25/0.2, 37/0.8 | 37/16 | 447 |
| C-2 | 70/30 | 100/0, $CaHPO_4$ | 25/0.2, 37/0.7 | 37/16 | 494 |
| C-3 | 70/30 | 50/50, $CaHPO_4$/ PHG 11 Lot 1 | 25/0.2, 37/6 | 37/64 | 317 |
| C-4 | 70/30 | 33/67, $CaHPO_4$/ CPG (Example 2) | 25/0.2, 37/6 | 37/64 | 351 |
| C-5 | 70/30 | 67/33, $CaHPO_4$/ CPG | 25/0.2, 37/6 | 37/64 | 442 |
| C-6 | 70/30 | 50/50, $CaHPO_4$/ $K_2HPO_4$ dibasic | 25/0.2, 37/6 | 37/64 | — |
| C-7 | 70/30 | 50/50, $CaHPO_4$/ $KH_2PO_4$ monobasic | — | 25/0.2 | — |
| C-8 | 70/30 | 95/5, CPG/ $K_2HPO_4$ dibasic | 25/0.2 | 37/64 | 386 |
| C-9 | 70/30 | 95/5, $CaHPO_4$/ $K_2HPO_4$ dibasic | — | 25/0.1 | — |
| C-10 | 70/30 | 97.5/2.5, $CaHPO_4$/ $K_2HPO_4$ dibasic | 25/0.1 | 37/0.1 | 560 |
| C-11 | 70/30 | 90/10, CPG/ $K_2HPO_4$ dibasic | 25/0.2 | 37/16 | 312 |

TABLE I-continued

Composition of Composite Precursors, Curing Conditions, and
Weight Average Molecular Weight ($M_w$) of Polymeric Matrix

| | Composite | | | | |
|---|---|---|---|---|---|
| | Precursor Compositions | | Curing Conditions | | Polymeric |
| | Inorganics/ | Weight Ratio of | Temp/Time, ° C./Hour | | Matrix |
| Number | MPC Mg/mL | Inorganic Component | Partial Curing | Full Curing | $M_w$, (kDa) |
| C-12 | 70/30 | 80/20. CPG/$K_2HPO_4$ dibasic | 25/0.2 | 37/16 | — |
| C-13 | 70/30 | 60/40, CPG/$K_2HPO_4$ dibasic | — | 25/0.1 | — |
| C-14 | 70/30 | 70/30, CPG/$K_2HPO_4$ dibasic | 25/0.2 | 37/3 | 416 |
| C-15 | 55/46 | 100/0, $CaHPO_4$ | — | 37/16 | 571 |
| C-16 | 50/50 | 99/1, $CaHPO_4$/PG-C[a] | — | 37/16 | 500 |
| C-17 | 50/50 | 95/5, $CaHPO_4$/PG-H[b] | — | 37/0.5 | 495 |
| C-18 | 50/50 | 95/5, $CaHPO_4$/chitosan | — | 37/0.3 | 452 |

[a]PG-C = micronized carboxy-terminated, low molecular polyglycolide made by ring-opening polymerization of glycolide in the presence of glycolic acid as the initiator according to the teaching of U.S. Pat. No. 5,612,052.
[b]PG-H = micronized hydroxy-terminated, low molecular weight polyglycolide made under similar conditions to those used in preparing PG-C with the exception of using trimethylene glycol as the initiator.

TABLE II

Aging of Composite Specimens in Deionized Water
at 50° C.: pH Decrease and Weight Loss Data

| Composite Number | Initial Mass (mg) | Decrease in pH over 10 Days | Mass Loss over 10 Days |
|---|---|---|---|
| C-1 | 115.6 | 1.8 | 25% |
| C-2 | 284.9 | 1.5 | 21% |
| C-3 | 83.2 | 1.1 | 20% |
| C-4 | 404 | 2.0 | 16% |
| C-5 | 148.9 | 1.8 | 11% |
| C-8 | 166.7 | 1.6 | 29% |

EXAMPLES 4 TO 16

Formation and Characterization of Composites C-2 to C-18

Composites C-2 to C-18 were prepared under conditions similar to those used in Example 3 for composite C-1, with the exception of using specific curing schemes as noted in Table I. The C-2 to C-14 composites were characterized for weight loss as described in Example 3. Typical weight loss data are summarized in Table II.

EXAMPLE 17

Testing of Leachable Components of Incubated Composites for Effect on Cell Viability Human fetal osteoblasts were seeded in 24-well plates at a density of $3.1 \times 10^4$ cells/cm$^2$ and maintained under standard cell culture conditions (that is a 37° C., humidified, 5% $CO_2$/95% air environment) for 24 hours. At that time, supernatant aqueous medium of the water-incubated composites (as described in Example 3 for the weight loss studies) was sterile-filtered and added to the osteoblast culture medium (1% volume). Controls were cells maintained under the same conditions, but only sterile water was added (1% volume). After 24 hours, MTS assay was used to determine cell viability.

EXAMPLE 18

Effect of Water Soluble Components of Aged Samples of the Incubated Composites

After removing the specimens incubated at 50° C. for 10 days in deionized water (see Example 3), aliquots of the water-soluble components were used to test their effect on osteoblast viability as described in Example 17, and all tested specimens associated with C-1, C-2, C-3, C-4, C-5, and C-8 from Table II were shown to have practically no detrimental effect on the osteoblast. The cell viability after 24 hours ranged about 90% to 100%.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicants hereby disclose all subranges of all ranges disclosed herein. The subranges are also useful in carrying out the present invention.

What is claimed is:

1. An absorbable, self-setting, bioactive composite comprising a matrix comprising a methoxypropyl cyanoacrylate, the matrix filled with a filler comprising anhydrous dibasic calcium phosphate microparticles, the composite comprising at least 20 percent by weight of the filler to volume of the composite, the matrix further containing polymeric microparticles comprising an anionic polymerization mediator.

2. An absorbable, self-setting, bioactive composite as set forth in claim 1 wherein the matrix further comprises ethylcyanoacrylate.

3. An absorbable, self-setting, bioactive composite as set forth in claim 1 wherein the filler further comprises at least one material selected from the group consisting of $K_2HPO_4$, $KH_2PO_4$, $Na_2HPO_4$, $NaH_2PO_4$, and an absorbable phosphate glass.

4. An absorbable, self-setting, bioactive composite as set forth in claim 3 wherein the absorbable phosphate glass is derived from CaO, $P_2O_5$, and at least one oxide selected from the group consisting of $K_2O$, $Na_2O$, ZnO, and $SiO_2$.

5. An absorbable, self-setting, bioactive composite as set forth in claim 1 further including at least one absorbable polymeric viscosity modifier selected from the group consisting of copolyesters of cyclic lactones, polyalkylene carbonates, polyalkyl cyanoacrykates, copolymeric cyanacrylates, and polymeric alkoxyalkyl cyanoacrylates.

6. An absorbable, self-setting, bioactive composite as set forth in claim 1 wherein the anhydrous dibasic calcium phosphate microparticles are capable of the controlled release of $(PO_4)^{-3}$ and $Ca^{+2}$ for promoting bone mineralization.

7. An absorbable, self-setting, bioactive composite as set forth in claim 1 wherein the anhydrous dibasic calcium phosphate microparticles are capable of the controlled release of $Zn^{+2}$ for accelerating bone growth.

8. An absorbable, self-setting, bioactive composite as set forth in claim 1 comprising at least one bone growth promoter selected from the group consisting of bone morphogenic protein (BMP), fibroblast-derived growth factors (FGF), and functionally similar oligopeptides and recombinant products.

9. An absorbable, self-setting, bioactive composite as set forth in claim 1 further comprising as least one bioactive agent selected from the group consisting of antimicrobial agents and anti-inflammatory agents.

10. An absorbable, self-setting, bioactive composite as set forth in claim 1 for use in applications selected from the group consisting of those involving tooth sockets, non-union bones, bone prostheses, osteoporotic bones, intervertebral spaces, alveolar ridges, facial and cranial fracture and defects, internal fracture fixation, artificial joint replacement, and infected bones.

11. An absorbable, self-setting, bioactive composite as set forth in claim 1 wherein the polymerized cyanoacrylate monomer has a weight average molecular weight exceeding 300 kDa.

12. An absorbable, self-setting, bioactive composite as set forth in claim 1 wherein the anionic polymerization mediator comprises a carboxyterminated polyglycolide.

13. An absorbable, self-setting, bioactive composite comprising a matrix comprising a methoxypropyl cyanoacrylate, the matrix filled with a filler comprising anhydrous dibasic calcium phosphate microparticles, the composite comprising at least 20 percent by weight of the filler to volume of the composite, the matrix further containing polymeric microparticles comprising an anionic polymerization accelerator.

14. An absorbable, self-setting, bioactive composite as set forth in claim 13 wherein the anionic polymerization accelerator comprises a hydroxyl-terminated polyglycolide.

15. An absorbable, self-setting, bioactive composite as set forth in claim 13 wherein the anionic polymerization accelerator comprises chitosan.

* * * * *